United States Patent [19]
Clement

[11] Patent Number: 5,505,210
[45] Date of Patent: Apr. 9, 1996

[54] LAVAGE WITH TISSUE CUTTING CANNULA

[75] Inventor: Thomas P. Clement, Bloomington, Ind.

[73] Assignee: Mectra Labs, Inc., Bloomfield, Ind.

[21] Appl. No.: 60,423

[22] Filed: May 11, 1993

Related U.S. Application Data

[63] Continuation-in-part of Ser. No. 956,601, Oct. 5, 1992, Pat. No. 5,335,671, which is a continuation-in-part of Ser. No. 830,580, Feb. 4, 1992, Pat. No. 5,409,013, which is a continuation-in-part of Ser. No. 580,945, Sep. 11, 1990, abandoned, which is a continuation-in-part of Ser. No. 432,084, Nov. 6, 1989, Pat. No. 5,019,054.

[51] Int. Cl.⁶ .................................................. A61B 10/00
[52] U.S. Cl. ............................ 128/753; 604/22; 606/170
[58] Field of Search .................................. 128/751–754; 606/167, 170

[56] References Cited

U.S. PATENT DOCUMENTS

| | | |
|---|---|---|
| 628,907 | 7/1899 | Hart . |
| 786,215 | 3/1905 | Hepnar .................................. 604/32 |
| 811,111 | 1/1906 | Wegefarth . |
| 1,585,934 | 5/1926 | Muir . |
| 2,437,329 | 3/1948 | Moore . |
| 2,708,437 | 5/1955 | Hutchins . |
| 2,715,899 | 8/1955 | MacLean . |
| 2,812,765 | 11/1957 | Tofflemire . |
| 3,012,752 | 12/1961 | Buck ...................................... 604/248 |
| 3,081,770 | 3/1963 | Hunter . |
| 3,109,426 | 11/1963 | Noonan . |
| 3,157,201 | 11/1964 | Littmann ................................ 604/32 |
| 3,173,414 | 3/1965 | Guillant . |
| 3,434,691 | 3/1969 | Hamilton .............................. 604/248 |
| 3,467,082 | 9/1969 | Gilbert . |
| 3,735,751 | 5/1973 | Katz . |
| 3,783,900 | 1/1974 | Waldbillig . |
| 3,788,602 | 1/1974 | Kitzie . |
| 3,794,032 | 2/1974 | Derouineau . |
| 3,833,000 | 9/1974 | Bridgman . |

(List continued on next page.)

FOREIGN PATENT DOCUMENTS

| | | |
|---|---|---|
| 2332743 | 7/1977 | France . |
| 3528656 | 7/1986 | Germany . |
| 4120329 | 1/1992 | Germany . |
| 991478 | 5/1965 | United Kingdom . |
| WO81/03125 | 11/1981 | WIPO . |

OTHER PUBLICATIONS

K. Semm, "Pelviscopy–Operative Guidelines", Kiel, Germany, 1988, pp. 53–54.
Pentax Precision Instrument Corp., "Gastrofiberscope", Surgical Products, Mar. 190, vol. 9, No. 6, p. 13.
Storz, "Laparoscopic Cholecystectomy for the General Surgeon—Its Time has Come", Surgical Products, May 1990, vol. 9, No. 6, p. 13.
Pentax Precision Instrument Corp., "GI Fiberscopes", Surgical Products, May 1990, vol. 9, No. 6, p. 13.
Healthco International Handbook, 1990, p. 116.
Storz The World of Endoscopy, Semm Instruments for Operative Pelviscopy, 4th Edition, Mar. 1987, pp. 1–4.
Richard Wolf cat. pg. and sketch/ admitted prior art Oct. 1989.
American Surgical Instruments, Inc., "Nexhat–Dorsey Disposable Hydro–Dissection Trumpet Valve", 3 Sheets, Mar. 19, 1990.
Richard Wolf, "The Complete Endoscopy Manufacture", Surgical Products, May 1990. vol. 9, No. 6, p. 20.
Johnson & Johnson Medical Inc., "CIDEX is safe for scopes. Don't take our word for it.", Surgical Products, May 1990, vol. 9, No. 6, p. 25.

(List continued on next page.)

Primary Examiner—Max Hindenburg
Attorney, Agent, or Firm—Barnes & Thornburg

[57] ABSTRACT

The present invention relates to an irrigation and suction lavage assembly for irrigation, suction, and removal of body tissue. The assembly includes a rigid conduit piece, an inner cannula, a movable outer cannula with a cutter, and an independently movable actuated valve to control irrigation and suction.

48 Claims, 8 Drawing Sheets

U.S. PATENT DOCUMENTS

| | | | |
|---|---|---|---|
| 3,834,372 | 9/1974 | Turney. | |
| 3,837,345 | 9/1974 | Matar. | |
| 3,853,127 | 12/1974 | Spademan. | |
| 3,902,498 | 9/1975 | Niederer. | |
| 3,957,082 | 5/1976 | Fuson et al.. | |
| 3,994,287 | 11/1976 | Turp et al.. | |
| 3,995,619 | 12/1976 | Glatzer. | |
| 4,011,869 | 3/1977 | Seiler, Jr.. | |
| 4,016,881 | 4/1977 | Rioux et al.. | |
| 4,037,599 | 7/1977 | Raulerson | 128/240 |
| 4,043,322 | 8/1977 | Robinson. | |
| 4,073,297 | 2/1978 | Kopp. | |
| 4,079,737 | 3/1978 | Miller. | |
| 4,099,529 | 7/1978 | Peyman | 128/305 |
| 4,111,207 | 9/1978 | Seiler, Jr. | 128/305 |
| 4,173,328 | 11/1979 | Karbo | 251/309 |
| 4,177,814 | 12/1979 | Knepshield et al. | 128/348 |
| 4,198,959 | 4/1980 | Otani | 128/5 |
| 4,210,146 | 7/1980 | Banko | 128/305 |
| 4,230,128 | 10/1980 | Aramayo | 128/763 |
| 4,240,411 | 12/1980 | Hosono | 128/4 |
| 4,261,357 | 4/1981 | Kontos. | |
| 4,280,498 | 7/1981 | Jensen. | |
| 4,282,873 | 8/1981 | Roth. | |
| 4,282,884 | 8/1981 | Boebel | 128/751 |
| 4,299,217 | 11/1981 | Sagae et al.. | |
| 4,314,560 | 2/1982 | Helfgott et al. | 128/305 |
| 4,314,586 | 2/1982 | Folkman | 251/368 |
| 4,379,458 | 4/1983 | Bauer et al. | 604/264 |
| 4,397,355 | 8/1983 | Doblar et al. | 604/32 |
| 4,400,168 | 8/1983 | Buechel et al. | 604/48 |
| 4,414,974 | 11/1983 | Dotson et al. | 128/305 |
| 4,430,081 | 2/1984 | Timmermans | 604/256 |
| 4,443,220 | 4/1984 | Hauer et al. | 604/408 |
| 4,445,517 | 5/1984 | Feild | 128/752 |
| 4,468,216 | 8/1984 | Muto | 604/43 |
| 4,491,132 | 1/1985 | Aikins | 128/305 |
| 4,512,344 | 4/1985 | Barber | 128/755 |
| 4,519,385 | 5/1985 | Atkinson et al. | 604/27 |
| 4,531,935 | 7/1985 | Berryessa | 604/55 |
| 4,540,156 | 9/1985 | Cross | 251/309 |
| 4,552,146 | 11/1985 | Jensen et al. | 128/305 |
| 4,553,957 | 11/1985 | Williams et al. | 604/43 |
| 4,553,964 | 11/1985 | Sasaki | 604/248 |
| 4,566,480 | 1/1986 | Parham | 604/32 |
| 4,568,332 | 2/1986 | Shippert | 604/119 |
| 4,577,629 | 3/1986 | Martinez | 604/22 |
| 4,581,014 | 4/1986 | Millerd et al. | 604/80 |
| 4,589,414 | 5/1986 | Yoshida et al. | 128/305 |
| 4,593,717 | 6/1986 | Levasseur. | |
| 4,595,005 | 6/1986 | Jinotti | 604/32 |
| 4,642,090 | 2/1987 | Utrata | 604/22 |
| 4,642,097 | 2/1987 | Siposs | 604/118 |
| 4,643,197 | 2/1987 | Greene et al. | 128/762 |
| 4,644,951 | 2/1987 | Bays | 604/22 |
| 4,645,496 | 2/1987 | Oscarsson | 128/673 |
| 4,648,868 | 3/1987 | Hardwick et al. | 604/32 |
| 4,651,753 | 3/1987 | Lifton | 128/751 |
| 4,654,027 | 3/1987 | Dragan et al. | 604/99 |
| 4,662,871 | 5/1987 | Rafelson | 604/119 |
| 4,667,927 | 5/1987 | Oscarsson | 251/209 |
| 4,674,500 | 6/1987 | DeSatnick | 604/22 |
| 4,676,242 | 6/1987 | Doi | 128/303.1 |
| 4,681,123 | 7/1987 | Valtchev | 128/753 |
| 4,690,672 | 9/1987 | Veltrup | 604/43 |
| 4,692,140 | 9/1987 | Olson | 604/40 |
| 4,702,260 | 10/1987 | Wang | 128/753 |
| 4,708,147 | 11/1987 | Haag | 128/753 |
| 4,715,360 | 12/1987 | Akui et al. | 128/4 |
| 4,735,606 | 4/1988 | Davison | 604/28 |
| 4,758,235 | 7/1988 | Tu | 604/248 |
| 4,793,359 | 12/1988 | Sharrow | 128/658 |
| 4,807,666 | 2/1989 | Morse | 251/309 |
| 4,808,155 | 2/1989 | Mahurkar | 604/43 |
| 4,810,244 | 3/1989 | Allen | 604/44 |
| 4,881,550 | 11/1989 | Kothe | 128/752 |
| 4,911,202 | 3/1990 | Nelson | 137/595 |
| 4,925,450 | 5/1990 | Imonti et al. | 604/240 |
| 4,932,957 | 6/1990 | Zwick | 606/160 |
| 4,958,621 | 9/1990 | Topel et al. | 128/4 |
| 4,966,551 | 10/1990 | Betush | 604/32 |
| 5,019,054 | 5/1991 | Clement et al. | 604/32 |
| 5,053,044 | 10/1991 | Mueller et al. | 604/96 |
| 5,078,688 | 1/1992 | Lobodzinski et al. | 604/164 |
| 5,273,524 | 12/1993 | Fox et al. | 604/21 |
| 5,275,609 | 1/1994 | Pingleton et al. | 606/170 |

OTHER PUBLICATIONS

Pentax®, "Pentax® PNEII Bronchofiberscopes", Surgical Products, May 1990, vol. 9, No. 6, p. 44.

Pentax Precision Instrument Corp., "Therapeutic Gastrofiberscope with Water Jet", Sep. 1990, vol. 10, No. 1, p. 39.

Cabot Medical, "Suction/Irrigation Probe", Surgical Products, Nov. 1990, vol. 10, No. 11, p. 29.

EndoDynamics, Inc., "Aspiration Device", Surgical Products, Nov. 1990, vol. 10, No. 11, p. 30.

"Irrigation/Aspiration Probe", Surgical Products, Sep. 1990, vol. 10, No. 1, p. 28.

Cabot Medical, "Larparoscopic Cholecystectomy From the Company Who Knows Laparoscopy", Surgical Products, Jan. 1991, vol. 10, No. 3, p. 4.

Olympus, "The Olympus Laparoscopic Cholecystectomy System: Resolution for Gallstones, with the leader in High–Resolution Optics", Surgical Products, Jan. 1990, vol. 10, No. 3, p. 8.

Apple Medical, "Hunt/Reich Secondary Cannula", Surgical Products, May 1991, vol. 10, No. 7, p. 5.

Baxter Healthcare Corp., "Infusion Pump", Surgical Products, Jun. 1991, vol. 10, No. 8, p. 32.

Core Dynamics™Inc., "Disposable Trocar with Reusable Cannula", Surgical Products, Jun. 1991, vol. 10, No. 8, p. 4.

Dexide catalog page and sketch 1991.

Halkey Roberts catalog 1990 3 pages.

LAVAGE WITH TISSUE CUTTING CANNULA

This is a continuation in part application of U.S. Application Ser. No. 07/956,601, to Clement, filed Oct. 5, 1992, now U.S. Pat. No. 5,335,671 which is a continuation in part application of U.S. Ser. No. 07/830,580, to Clement, filed Feb. 4, 1992, now U.S. Pat. No. 5,408,013 which is a continuation in part of U.S. Ser. No. 07/580,945, to Clement et al., filed Sep. 11, 1990, now abandoned which is a continuation in part of U.S. Ser. No. 07/432,084, filed Nov. 6, 1989 and now U.S. Pat. No. 5,019,054, to Clement et al., issued May 28, 1991.

The present invention relates to irrigation and suction lavage assemblies and particularly to assemblies having inner and outer concentric cutting cannulas with tip ends configured to allow cutting. More particularly, the present invention relates to a movable cutting cannulas of sufficient size to allow the passage therethrough of other surgical instruments wherein the outer cannula is movable relative to the inner cannula to cut tissue.

Removal of tissue from a patient's body for disposal or analysis is commonly required in surgical procedures. Typically, cutting instruments have been used to separate small portions of tissue from the patient's body, and grasping or suction devices have been used to retrieve the tissue. For removal of small organs or tissue in laparoscopic or endoscopic surgical procedures, combination instruments that combine cutting and suction functions are known. Such dual function cutting/suction instruments can include a cutting instrument disposed inside a tube having a notch or other opening to permit the cutting instrument to have selective access to body tissue.

Unfortunately, the use of such dual function cutting/suction instruments often requires the use of an additional instrument to provide for irrigation of the operating site. Morover, if the cutting of tissue during the procedure results in a bleeder, yet another instrument is required to cauterize the wound. The juggling of a multitude of instruments by the surgeon is awkward at best and, in the extreme, can become dangerous.

A single assembly that allows the irrigation, cutting, and suction functions to be carried out single-handedly by a surgeon would be highly desirable. If the assembly provided for the employment of an electro-cautery device, that assembly would be a substantial improvement over conventional cutting/suction assemblies.

The present invention provides a single assembly with provisions for irrigating an operating site, cutting tissue, and removing irrigation fluid and the cut body tissue by suction during laparoscopy surgery. The irrigation and suction lavage assembly includes provisions for sealably inserting a surgical instrument, such as a electro-cauterizer, to be presented at the operating site. Preferably, the entire assembly is only used once, and is constructed from low-cost, easily disposable materials.

According to the present invention, the lavage assembly includes a conduit piece and inner and outer cannulas. The inner cannula has a proximal end coupled to the conduit piece and a distal end. The inner cannula defines an interior region and includes first means for cutting tissue formed at the distal end. The outer cannula includes a distal end and second means for cutting tissue formed adjacent the distal end.

The inner cannula is coaxially positioned inside the outer cannula and the first and second means for cutting are axially positioned to cut tissue in response to movement of the outer cannula. The assembly further includes valve means for controlling the flow of irrigation fluid and cut body tissue through the inner cannula and the conduit piece.

Figures 7, 8, 9, 10:
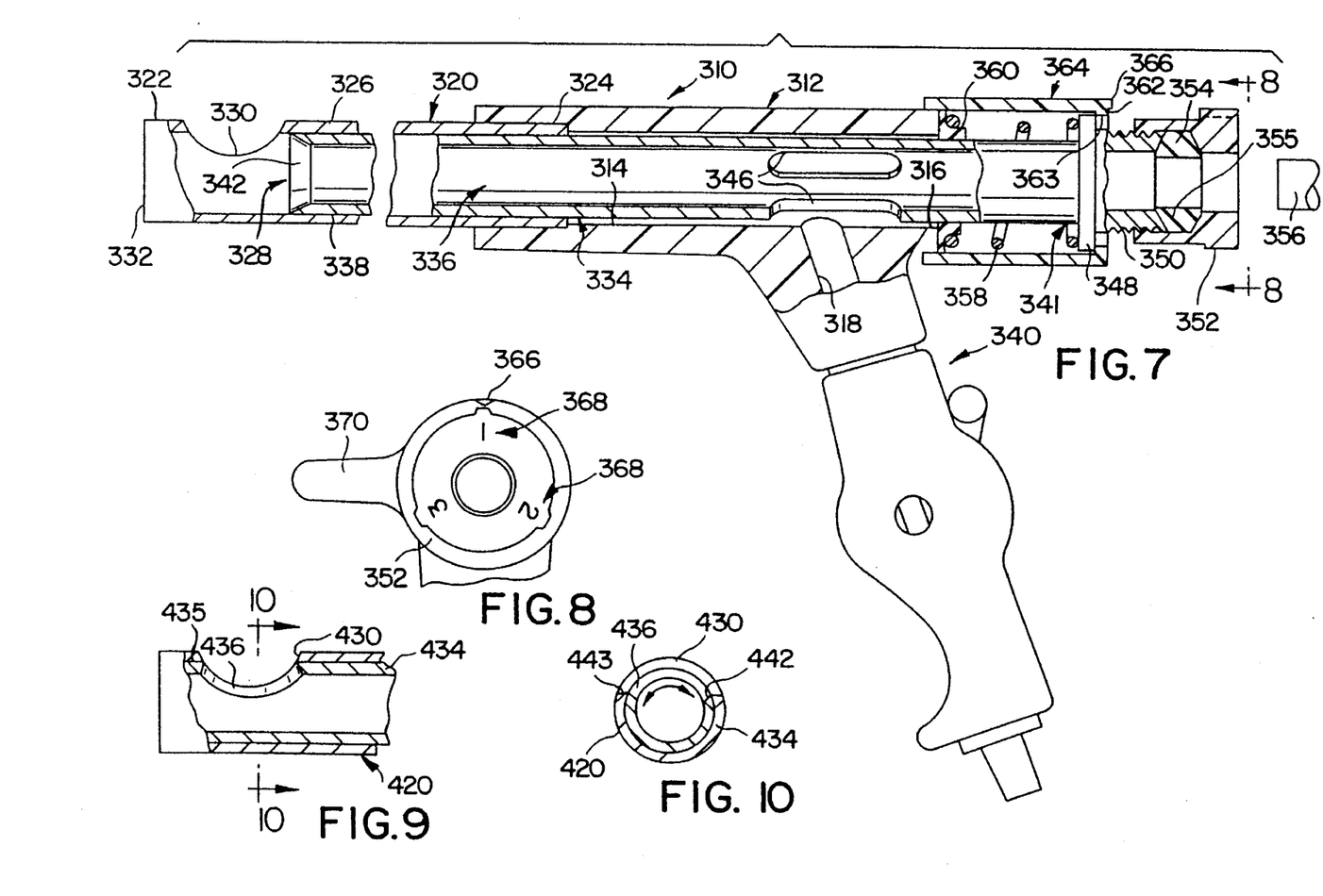
FIG. 7 is a partial sectional view of an alternative embodiment of a tissue removal assembly wherein a reciprocating cannula has a cutting tip and extends the length of the outer cannula and provides a passageway for other surgical instruments to be positioned adjacent the tissue to be removed.
FIG. 8 is an end view of the embodiment of FIG. 7, as seen from the right, showing numerical indicia and an indexing mark.
FIG. 9 is a partial view of an alternative embodiment of the tip of the apparatus having a notch positioned adjacent the distal end of the inner cannula, wherein the notches in the inner and outer cannulas are configured to be rotated relative to each other to cut tissue.
FIG. 10 is a cross-sectional view taken along lines 10—10 of FIG. 9 showing reversed bevelled edges in the inner and outer cannula notches to provide a scissors-type cutting action.

According to one aspect of the invention, the outer cannula is resiliently coupled to the conduit piece for reciprocating movement relative to the inner cannula and includes means for engaging a digit of the surgeon's hand to permit one-handed reciprocation of the outer cannula by the surgeon. It will be appreciated that the outer cannula can be rotated relative to the inner cannula, as shown in FIGS. 9 and 10 in relation to another embodiment. The engaging means includes resilient means for coupling the engaging means to the conduit piece and a trigger for engaging a digit of a surgeon's hand. The trigger is configured to be pulled toward the conduit piece and released to reciprocate the outer cannula. When the trigger is released, the resilient means urges the outer cannula away from the conduit piece, cutting tissue in the process.

In an alternative embodiment of the invention, the engaging means includes an outrigger for engaging a digit of a surgeon's hand. The outrigger is pushed away from the conduit piece and released to reciprocate the outer cannula. The resilient means urges the outer cannula toward the conduit piece in response to release of the outrigger, cutting tissue in the process.

According to another aspect of the invention, first means for breachably sealing the inner cannula is positioned in the proximal end of the inner cannula. Illustratively, the first means for sealing is a duckbill flap valve that allows a surgical instrument to be sealingly inserted into the inner cannula.

According to yet another aspect of the invention, the conduit piece includes a channel, and second means for breachably sealing the channel is coupled to the channel of the conduit piece. In an illustrative embodiment, the second means for sealing includes a compressible annular ring that allows a surgical instrument to be sealingly inserted into the inner cannula through the channel.

According to still another aspect of the invention, the valve means includes a valve body coupled to the conduit piece and housing a valve therein, wherein the conduit piece includes second and third channels in fluid communication with the first channel in the conduit piece and the valve body is shaped to have a manually grippable body to form a pistol grip with the conduit piece. The valve body defines a fourth channel that is in fluid communication with the first channel in the conduit piece.

By providing an assembly with concentric cutting cannulas for cutting tissue, valve means for controlling the flow of irrigation fluid and the removal of irrigation fluid and body tissue, and sealing means to allow a surgical instrument, such as an electro-cautery device, to be presented to the operating site, the present invention eliminates the need for separate irrigating instruments and cauterizing instruments. Consequently, fewer instruments are required to perform a procedure, thereby eliminating the costs associated with those instruments as well as easing the surgeon's workload. Moreover, by eliminating the need for additional instruments, the present invention also reduces the time necessary for the completion of the procedure by eliminating the time necessary to swap instruments.

Other objects and advantages of the invention will become apparent from the following description of a preferred embodiment presently perceived as the best mode for practice of the invention and consideration of the accompanying drawings.

DETAILED DESCRIPTION OF THE DRAWINGS

Figures 1, 2:
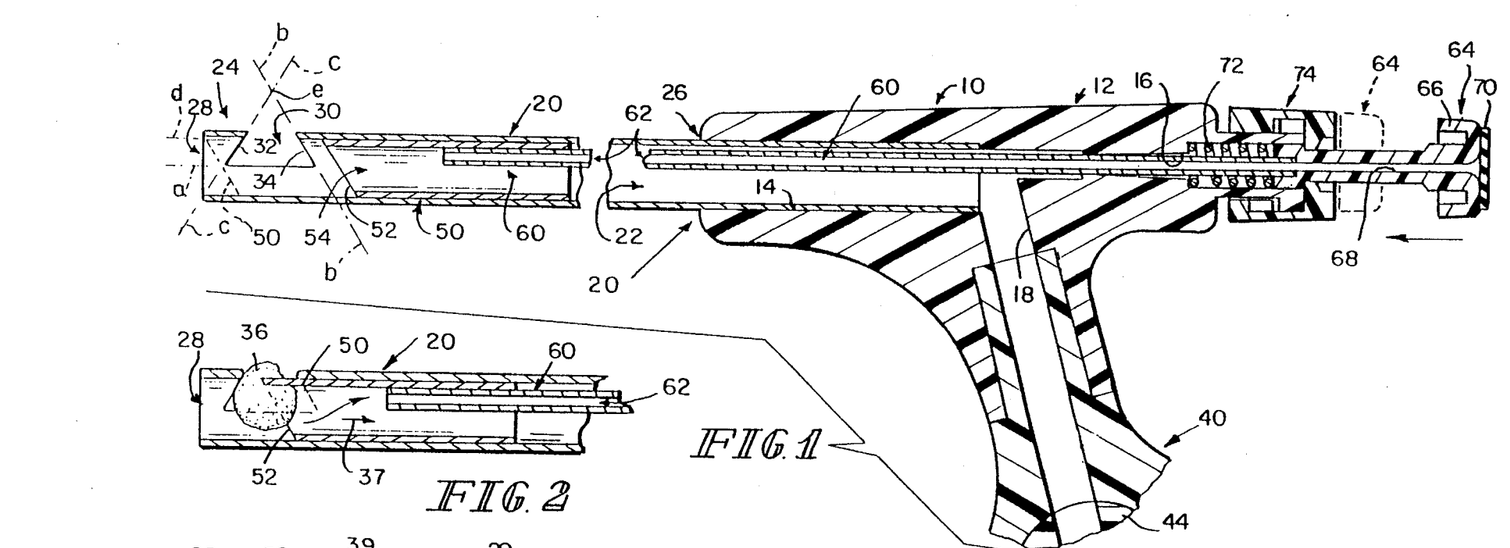
FIG. 1 is a cross sectional side view of a tissue removal assembly including a cannula having a notch defined in its distal end, a cutter movably positioned inside the cannula, and a handheld rotary valve (partially shown) extending from the conduit piece to provide a pistol-type grip.
FIG. 2 is a sectional side view of the distal end of the cannula illustrated in FIG. 1, showing the position of tissue caught by oppositely directed catches and maneuvered into the cannula interior through the notch to allow tissue dissection and removal for analysis or disposal of small pieces of tissue.

As best illustrated in FIG. 1, a tissue removal assembly 10 useful for laparoscopic, endoscopic, or other surgical procedures includes a conduit piece 12 interconnecting a cannula 20 and a handheld rotary valve 40. Suitable handheld rotary valves are described in U.S. Pat. No. 5,019,054, to Clement et al., issued May 28, 1991, and assigned to Mectra Labs, Inc., the disclosure of which is herein incorporated by reference. Typically, a surgeon supports the assembly 10 with one hand holding the handheld rotary valve 40, leaving the other hand free for manipulation of other instruments.

The tissue removal assembly 10 is useful for removing small organs, scar tissue, growths, biopsy samples, or other tissue from a patient's body. The tissue removal assembly 10 can also be used to destroy tissue at an operative site by laser ablation, or can alternatively be used to cut away tissue for later analysis or disposal.

In preferred embodiments, the tissue removal assembly 10 is disposed of after a single use, minimizing problems related to sterilization, storage, and maintenance of reusable instruments. Construction from low cost, easily incinerated or disposed of materials, which may include molded plastics, is contemplated.

The conduit piece 12 is formed to internally define a first channel 14, a second channel 16, and a third channel 18. All three channels 14, 16, and 18 substantially define respective cylindrical volumes, with first channel 14 having a slightly greater inner diameter than the second channel 16. The third channel 18 has an inner diameter intermediate between that of the first and second channels 14 and 16. The first channel 14 and second channel 16 are connected in fluid communication, and are colinearly defined to allow straight passage therethrough of linearly extending objects. The third channel 18 is also in fluid communication with channels 14 and 16, and connects substantially perpendicular to and between the channels 14 and 16. As will be appreciated with reference to FIG. 1, the interconnections between the channels 14, 16, and 18 can be characterized as a "T-type" connection. However, provision of "Y"-type connections or other arrangements known in the art for fluid interconnection of channels 14, 16, and 18 is contemplated.

As shown in FIG. 1, the cannula 20 extends longitudinally in a straight line, although curved, bent, flexible, or other conventional cannula designs are also contemplated. The cannula 20 has a distal end 24 for insertion into a patient's body and a proximal end 26 connected to the conduit piece 12. The distal end 24 of the cannula 20 terminates in a tip opening 28 that allows ingress or egress of solids, liquids, or gasses from a cannula interior 22 defined by the cannula 20. The cannula interior 22 is defined between the respective distal and proximal ends 24 and 26 of the cannula 20 to accept and allow bidirectional passage therethrough of solids, liquids, or gasses. Fluids, instruments, or gasses can be introduced from the proximal end 26 for effective operation in a patient's body at the distal end 24, or fluid (blood, etc.), solids (such as tissue samples), or gasses (such as may be produced by laser ablation and vaporization) at the operating site can be withdrawn from the distal end 24 through the cannula interior 22.

The cannula 20 is dimensioned to conformably fit into the first channel 14 of the conduit piece 12, and is rigidly held in position by adhesives, welding, friction tight fit, or other suitable attachment mechanism to the conduit piece 12. Since the proximal end 26 of the cannula 20 is held within the first channel 14, fluid communication (as well as passage of medical instruments or tissue samples) is maintained between the second and third channels 16 and 18, and the cannula interior 22.

The distal end 24 of the cannula 20 is configured to assist in capture and retention of body tissue 36 at an operating site in a patient's body. As is illustrated in FIGS. 1 and 2, a notch 30 is defined in the distal end 24 of the cannula 20, immediately adjacent to the tip opening 28 of the cannula 20. Like the tip opening 28, the notch 30 allows access to the cannula interior 22. The notch 30 is cut in the cannula 20 to define a first catch 32 and an oppositely directed second catch 34. As illustrated in FIG. 1, the notch 30 is formed by removal of a portion of the distal end 24 of the cannula 20. Two cuts into cannula 20 are made along oppositely directed planes indicated by lines b and c (planes b and c both extend perpendicular to the page in the illustration). The cuts along planes b and c terminate at their respective intersection with longitudinally directed planes indicated by lines a and d (planes a and d also extend perpendicular to the page). When a line of intersection between planes b and c is defined outside the cannula 20 (the line extends perpendicular to the page and is represented by a point e), a dihedral angle bc between planes b and c is defined. Typically, the dihedral angle bc is between about 30 degrees and 150 degrees, and is illustrated in FIG. 1 as about 60 degrees.

In practice, the notch 30 and catches 32 and 34 can be easily formed by three cuts into the cannula 20 along planes a, b, and c. More complex cutting, forming, molding, or castings can also be used to provide catches of differing shape. In addition, instead of forming catches from the body of the cannula, it is also contemplated to provide oppositely directed catches attached or affixed to a cannula adjacent to a notch. Multiple catches or several notches may also be used to enhance tissue grabbing or retention effectiveness.

In operation, as illustrated in FIG. 2, catches 32 and 34 enhance tissue grabbing and holding effectiveness, allowing a surgeon to maneuver the distal end 24 to catch and hold a piece of body tissue 36. After body tissue 36 has been positioned in the notch 30, a cutter 50 can be moved forward from its position in the cannula interior 22 toward the distal end 24 of the cannula 20 to cut and/or assist in retaining tissue in the notch 30.

As illustrated in FIG. 1, the cutter 50 has a substantially tubular configuration, defining a cutter passageway 54 therethrough. In addition, the distally directed end of the cutter 50 has a sharpened edge 52. To enhance cutting efficiency, the sharpened edge 52 is created by a traverse, slanting, and non-perpendicular cut across the cutter 50. The resultant elliptically shaped cylinder edge is sharpened to give a beveled edge, with the bevel being directed inward toward the cannula interior 22. Of course, perpendicular cuts across a cutter to give a circular edge, or other cutter edge configurations apparent to those skilled in the art may be substituted for the illustrated cutter embodiment.

The cutter 50 is sized to snugly fit into the cannula interior 22, with its outer diameter being slightly less than the inner diameter of the cannula 20. As illustrated in FIG. 2, when tissue has been engaged by catches 32 and 34 and maneuvered into the cannula interior 22 through the notch 30, the cutter 50 is moved forward from its normal position on the proximal side of the notch 30 in the cannula interior 22, to a cutting position in the region of the notch 30 (position of cutter 50 indicated by dotted outline). When the cutter 50 passes through the cannula interior 22 to cover the region of the notch 30 (adjacent to tip opening 28) any tissue entrapped in the cannula interior 22 is severed by the sharpened edge 52. This severed, dissected tissue can be drawn by surgical instruments, or preferably by suction pressure, through the cutter passageway 54, toward the distal end 24 of the cannula interior 22, into the third channel 18 of the conduit piece 12 and through the handheld rotary valve 40 to a storage or disposal site.

The cutter 50 is moved by a movable assembly 64. The movable assembly 64 includes a button 66 that defines a passageway 68 therethrough. The passageway 68 is breachably sealed by seal 70 in adhesive or welded attachment to the button 66. A tube 60, having a tube interior 62, is attached to extend between the cutter 50 and the button 66. Movement of the button 66 toward the conduit piece 12 consequently causes the cutter 50 to move toward the distal end 24 of the cannula 20.

The cutter 50 is moved back toward the proximal end 26 of the cannula 20 by action of an expansion spring 72. The expansion spring 72 is biasably positioned between the conduit piece 12 and the button 66 to press the button 66 away from the conduit piece 12. When the button 66 is not manually pressed toward the conduit piece 12, this outward (away from the conduit 12) biased force is resisted by a block 74 attached to the conduit piece 12 and configured to partially surround button 66. The spring arrangement is configured to promote manually operated reciprocating motion, with the rest, or normal, position of the cutter 50 (attached by way of tube 60 to the button 66) selected to be on the proximal side of the notch 30, leaving the notch 30 normally open to accept body tissue. Of course, as those skilled in the art will appreciate, it is alternatively contemplated to reverse the biased spring direction, so that a cutter 50 is normally positioned on the distal side of the notch, with the cutter having its proximal edge sharpened.

Figure 3:
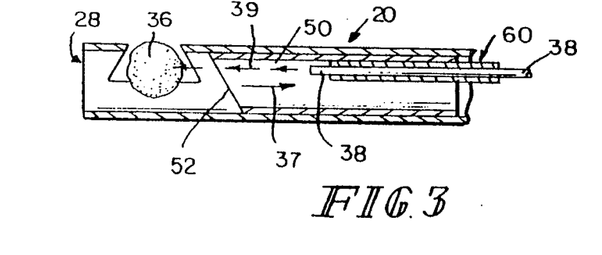
FIG. 3 is a sectional side view of the distal end of the cannula illustrated in FIGS. 1 and 2, showing the positioning of a fiber optic cable in a tube interior of a tube attached to the cutter, the fiber optic cable acting to convey laser energy for vaporization of tissue positioned in the cannula interior.

In addition to separation of tissue from a patient's body by cutting action of the cutter 50, tissue can optionally be removed by application of laser energy to ablate and vaporize tissue. As illustrated in FIG. 1 and FIG. 3, delivery of laser energy (indicated by arrows 39 in FIG. 3) to tissue 36 is enabled by passage of fiber optic cable 38 inserted, respectively, through breachable seal 70, passageway 68 of button 66 (seal 70 and button 66 illustrated in FIG. 1), and tube interior 62 of tube 60. In operation, the tissue 36 is maneuvered into position through the notch 30, and laser energy is transmitted through the fiber optic cable 38 from a laser light source (not shown) to vaporize the tissue 36.

Figure 4:
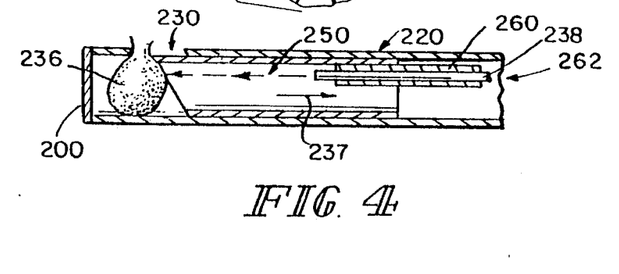
FIG. 4 is a sectional view of an alternative embodiment of a distal of the cannula illustrated in FIGS. 1–3, wherein the tip of the cannula is closed to present a laser energy absorbing or dissipating surface to reduce the risk of inadvertent burning or vaporization of tissue.

An alternative cannula tip embodiment suitable for dual mechanical cutter/laser removal of tissue is illustrated in FIG. 4. A cannula 220 (substantially similar to cannula 20) having a notch 230 therein is used to entrap tissue 236. The distal end of the cannula 220 is closed with a tip wall 200. The tip wall 200 can be coated or otherwise prepared to have a laser absorptive or dissipative surface that reduces back reflection of laser energy transferred through fiber optic cable 238 (positioned in tube interior 262 of tube 260) to the tissue 236. In operation, after the tissue 236 is firmly positioned in the notch 230, the cutter 250 can be moved forward to substantially cover the notch 230. This reduces escape of fumes or burned tissue into the patient's body. Of course, the cutter 250 can still alternatively be used without recourse to laser energy to dissect and remove tissue.

Figure 5:
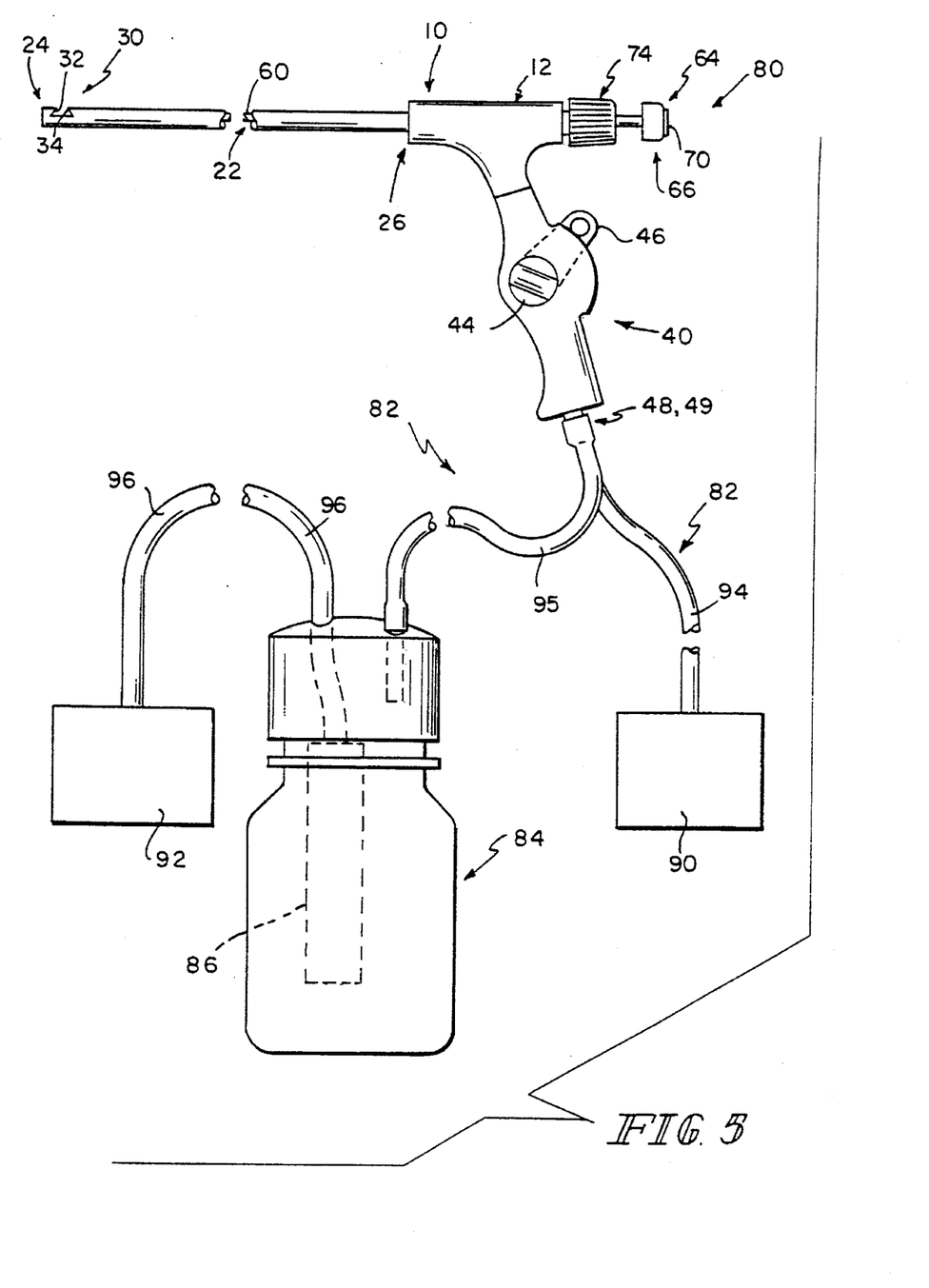
FIG. 5 is a schematic view of a tissue removal system, illustrating the tissue removal assembly of FIG. 1 connected to a tissue sample trap assembly that includes a tissue sample container connected to a vacuum source.

Dissected tissue or fumes from vaporized tissue are removed from the cannula by suction (indicated by arrow 37 in FIGS. 2-3, and arrow 237 in FIG. 4) produced by fluid connection to one of vacuum sources 90 and 92 illustrated in FIG. 5. As illustrated in FIG. 5, a tissue removal system 80 includes a tissue storage apparatus 82 connected to tissue removal assembly 10 such as previously described. The tissue storage apparatus 82 includes a sample container 84, conduits 94, 95, 96, and vacuum sources 90 and 92. Conduit 94 is connected in fluid communication between inlet 49 of the rotary valve 40 and vacuum source 90. Conduit 95 is connected in fluid communication between inlet 48 of the dual inlet port rotary valve 40 and vacuum source 92. Conduit 96 is connected to a screen 86 positioned inside sample container 84, allowing fluid communication between the sample container 84 and vacuum source 92 but limiting passage of solid tissue samples.

In operation, disposal of tissue samples entrained in the cannula interior 22 of the cannula 20 involves turning the handle 46 of the rotary valve 40 to bring the rotor 44 into a position that allows fluid communication between vacuum source 90 and cannula interior 22. Solid, liquid, or gas waste that is present in the cannula interior 22 are drawn by suction toward the proximal end 26 of the cannula 20, and through the third channel 18 into the rotary valve 40. The wastes continue through the conduit 94 and into the vacuum source 90 for disposal.

If samples of tissue are desired for analysis, the handle 46 of the rotary valve 40 is turned to bring the rotor 44 into a position that allows fluid communication between vacuum source 92 and cannula interior 22. A solid tissue sample dissected from a patient's body and present in the cannula interior 22 are drawn by suction toward the proximal end 26 of the cannula 20, and through the third channel 18 into the rotary valve 40. The sample is drawn by suction through the conduit 95 and into the sample container 84 for storage. Continued passage of the sample (not shown) through the conduit 96 and into vacuum source 92 is prevented by a screen 86 that allows fluid flow but prevents passage of tissue sample sized solids.

Figure 6:
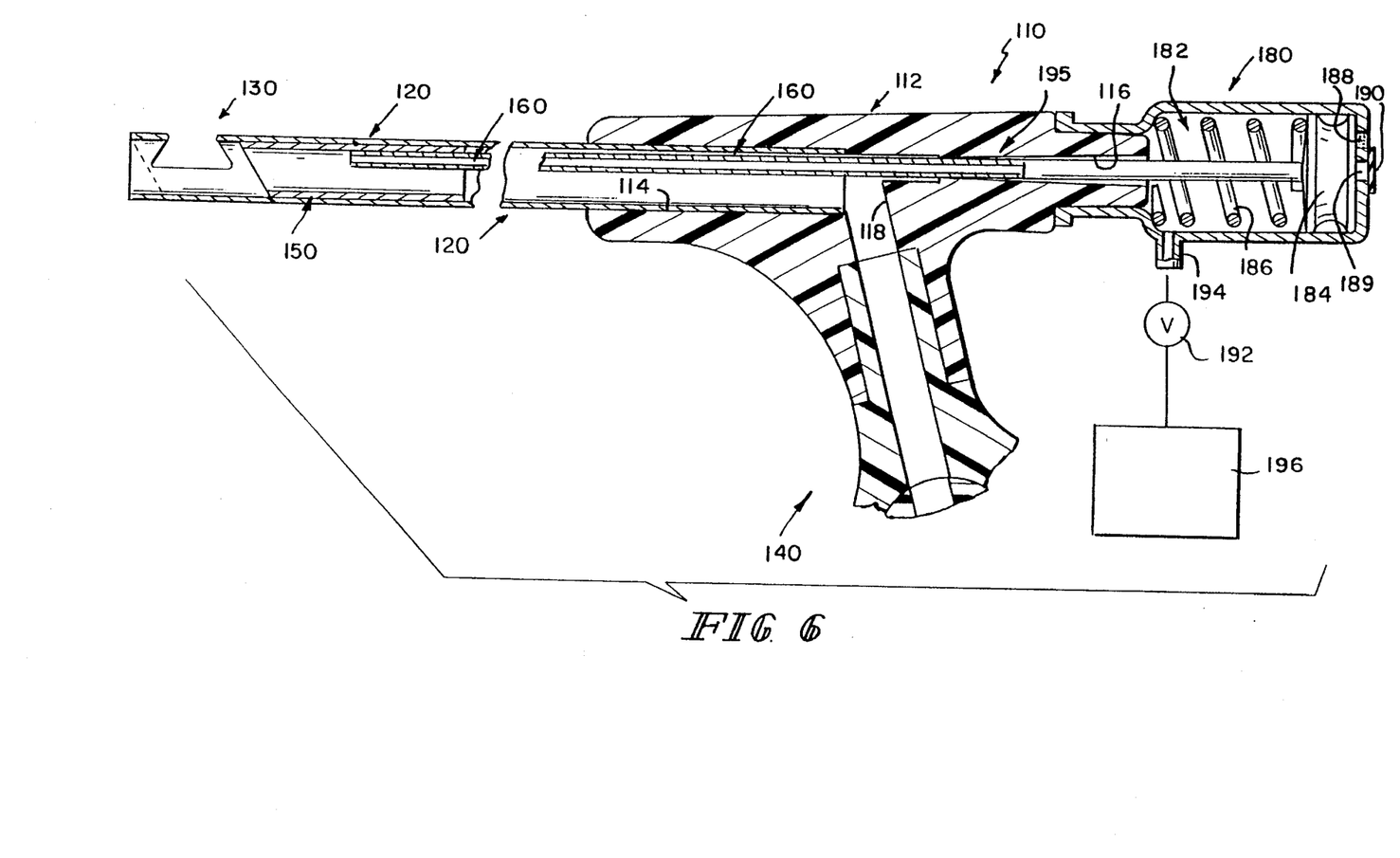
FIG. 6 is a sectional view of an alternative embodiment of the tissue removal assembly of FIGS. 1–3, wherein the movement of the cutter is controlled by a vacuum powered mechanism attached to the conduit piece and connected to reciprocatingly move the tube and attached cutter.

An alternative embodiment of the invention in which movement of a cutter is controlled by application and release of a vacuum is illustrated in FIG. 6. A tissue removal assembly 110 includes a cannula 120 connected to a conduit piece 112 and a valve 140. The conduit piece 112 is formed to define first, second and third channels 114, 116, and 118, with the cannula 120 being inserted into the conduit piece 112 to fit into first channel 114. In addition, like the embodiment of the invention illustrated in FIG. 1, a cutter 150 can be moved through the cannula 120 to alternately block notch 130 or allow passage through the notch 130 of body tissue (not shown).

The cutter 150 is attached to a tube 160 configured to support a fiber optic cable capable of transferring laser energy to an operative site. Although use of a laser is not always required, its ready availability allows a surgeon to select to use the laser alone, the cutter alone, or both the laser and the cutter as necessary to optimize surgical treatment.

The tube 160 passes through the cannula 120 and into conduit piece 112, where it passes in substantially gas tight sliding seal through neck 195 of the second channel 116. The sliding seal in neck 195 can optionally be enhanced by the use of lubricants or low frictional resistance polymeric coatings. Of course, as those skilled in the art will appreciate, breachable elastomeric seals, annular seals, or other conventional sliding seals can be used.

After passing through neck 195, the tube 160 enters chamber 182 of a vacuum powered mechanism 180. The vacuum powered mechanism 180 is a low cost, disposable mechanism attached to the conduit piece 112 to allow a surgeon to control movement of the cutter 150. The chamber 182 of the mechanism 180 is configured to define an air inlet 188, a passageway 189, and a vacuum port 194 for connection by way of valve 192 to a vacuum source 196. Valves such as described in U.S. Pat. No. 5,019,054, to Clement et al., issued May 28, 1991, are preferred, although of course other conventional valves or mechanisms for controlling application of vacuum and allowing admission of air into chamber 182 are also suitable. In other contemplated embodiments, a separate valve positioned between the chamber 182 and the vacuum source is not required. As those skilled in the art will appreciate, the vacuum source 196 can be directly controlled to provide pulsatile, oscillatory, or other predetermined suction action to withdraw air from the chamber 182.

The air inlet 188 defined by chamber 182 is normally open to atmosphere, and passageway 189 is sealed by a breachable seal 190 adhesively attached to the chamber 182. The chamber 182 is dimensioned to allow placement of helical spring 186 or other suitable energy storing resilient piece (e.g. leaf springs) into the chamber 182. The spring 186 is positioned between a sliding piston 184 and the conduit piece 112. As will be appreciated by those skilled in the art, the position of a spring or resilient piece in the chamber 182 can be varied to accommodate differing spring directions (i.e. biased to resist motion either away or toward the conduit piece 12). In addition, by providing suitable interconnections between the piston 184 and a spring, it is contemplated to mount the spring outside the chamber, rather than inside as illustrated.

The sliding piston 184 is positioned in sliding, gas tight movement in chamber 182. The piston 184 is attached to tube 160, and is configured to have a passageway therethrough (not shown) in fluid communication with the tube 160. Presence of the passageway through the piston 184 allows a surgeon to insert a fiber optic cable (not shown) through the seal 190 and passageway 189, and continue insertion through the passageway of piston 184 into tube 160 for positioning at the surgical site.

Operation of the assembly 110 is similar to operation of assembly 10 illustrated in FIG. 1, with the following difference in cutter actuation. Instead of manually pressing button 66 of assembly 10 to move the cutter 50, use of assembly 110 requires operating valve 192 to open a fluid connection between chamber 182 and vacuum source 196. Air present in chamber 182 rushes out through port 194, causing movement of the piston 184 (or other devices that move in response to pressure changes such as a diaphragm) toward the conduit piece 112. Movement of the piston 184 simultaneously compresses the spring 186 to store energy, and moves the cutter 150 (attached to the piston 184 by tube 160) forward through the notch 130 of the cannula 120, cutting any tissue contained therein. After the cutter has moved forward, the valve 192 can be moved to a position allowing influx of air at normal atmospheric pressure into the chamber 182, which in turn allows release of spring 186 and movement of the piston 184 and attached tube 160/cutter 150 away from the notch 130. The valve 192 can be moved to an open position to repeat the foregoing operation.

In the alternative embodiment of FIG. 7, the tissue removal assembly 310 includes a conduit piece 312 having first, second, and third channels 314, 316, and 318, respectively, with the third channel 318 attached to a vacuum source (not shown) through a handheld rotary valve 340. A suitable handheld rotary valve is described in U.S. Pat. No.

5,019,054 to Clement et al. The handheld rotary valve 340 is rigidly attached to the conduit piece 312 to form a pistol grip. Thus, by grasping the rotary valve 340, the surgeon has positive control of the placement and positioning of the distal end 322 of the cannula 320.

The first and second channels 314, 316 are coaxially aligned, and the third channel 318 joins the first and second channels 314, 316 at an angle to the axis. An outer cannula 320 has an open distal end 322, an open proximal end 324, and a side wall 326 defining a first interior region 328 that extends between the distal and proximal ends 322, 324, respectively. Proximal end 324 of the cannula 320 is dimensioned to conformably fit into the first channel 314 of the conduit piece 312, and is rigidly held in position by adhesives, welding, friction-tight fit, or other suitable attachment mechanism to the conduit piece 312. Since the proximal end 324 of the cannula 320 is held within the first channel 314, fluid communication is maintained between the second and third channels 316, 318, respectively, and the interior region 328. Moreover, the coaxial alignment of the first and second channels 314, 316, which illustratively are of the same general diameter, allows passage of medical instruments through the conduit piece to the open distal tip end 322 of the cannula 320.

The distal end 322 of the cannula 320 is configured to assist in capture and retention of body tissue at an operating site in a patient's body. A notch 330 is defined in the distal end 322 immediately adjacent the tip opening 332 of the cannula 320 and allows tissue to enter the interior region 328. The tip opening 332 allows medical instruments, such as a cauterizing device, that have been passed through the first and second channels 314, 316 and the outer cannula 320 to be positioned at the operating site.

An inner cannula 334 has an open distal end 338 and an open proximal end 341, and a second interior region 336 therebetween. The distal end 338 of the inner cannula 334 has a sharpened bevelled edge 342, with the bevel being directed inwardly toward the second interior region 336 as shown in FIG. 7.

The inner cannula 334 is sized to snugly fit into the first interior region 328. A plurality of longitudinal slots 346 are formed circumferentially around the inner cannula 334. The slots 346 are axially co-located with the junction between the first and second channels 314, 316, and the third channel 318. The slots 346 are sized and positioned to ensure that at least a portion of the third channel 318 of the conduit piece 320 is always in fluid communication with the second interior region 336 of the inner cannula 334. In order to avoid vacuum leaks between the inner cannula 334 and the second channel 316, an annular grommet 360 is configured to abut the proximal end of the second channel 316 and fit around the outside of the inner cannula 334. The inner cannula 334 also includes a spring-retaining flange 348 that extends radially outwardly from the proximal end 341 of the inner cannula 334.

An externally threaded annular projection 350 extends axially from the spring-retaining flange 348 in the direction away from the distal end 338 of the inner cannula 334. An internally threaded compression member 352 engages the externally threaded annular projection 350. A compressible cannula seal 354 having a central aperture 355 is disposed between the compression member 352 and the annular projection 350. Threading the compression member 352 onto the annular projection 350 squeezes the compressible seal 354 therebetween to close the central aperture 355.

When the compression member 352 is fully engaged with the annular projection 350, central aperture 355 is completely closed to restrict the entry of air or other contaminants into the second interior region 336. As the compression member 352 is unscrewed from the annular projection 350, the central aperture 355 opens to allow insertion of a medical instrument 356 into the second interior region 336 of the inner cannula 334.

A conduit piece extension member 364 is rigidly attached to the conduit piece 312 by welding, threading, or the like. A perimetral shoulder 362 is formed on the extension member 364 to extend inwardly toward the longitudinal axis of the inner cannula 334. The perimetral shoulder 362 defines an aperture 363 that is sized to permit axial movement of the annular projection 350 and the compression member 352 while blocking passage of the spring retaining flange 348 therethrough.

A return spring 358 is positioned between the annular grommet 360 and the spring-retaining flange 348. The return spring 358 urges the spring-retaining flange 348 into contact with the perimetral shoulder 362, which interferes with the axial movement of the spring-retaining flange 348. At the same time, the return spring 358 retains the annular grommet 360 in sealing engagement with the proximal end of the conduit piece 312. The perimetral shoulder 362 is axially positioned so as to maintain the sharpened edge 342 of the inner cannula 334 in a normal, or rest, position that is proximal to the notch 330 when the flange 348 is positioned against the shoulder 362.

Using a circular cross section for the outer cannula 320 and inner cannula 334 advantageously allows multiple cutting segments using the same inner cannula 334 by simply rotating the inner cannula 334 inside the outer cannula 320. When a first portion of the sharpened edge 342 becomes dulled by use, rotation of the inner cannula 334 presents a different portion of the sharpened edge 342 to tissue entrapped in the notch 330. Depending upon the size of the notch 330, a single inner cannula 334 can effectively have 2, 3, or more cutting portions of the sharpened edge 342.

As illustrated in FIG. 8, an indexing mark 366 can be formed on the proximal end of the conduit piece extension member 364. A numerical indicia 368 can be incorporated into the compression member 352, as illustrated in FIG. 9, to cooperate with the indexing mark 366. As the inner cannula 334 is rotated to present a different portion of the sharpened edge 342, the numerical indicia 368 provides a positive indication to the surgeon of the remaining unused portions of the sharpened edge 342.

In operation, the distal end 322 of the outer cannula 320 is inserted into the patient's body and maneuvered to position tissue to be excised through the notch 330 into the interior region 328. When the tissue is positioned inside the interior region 328, the surgeon pushes on the compression member 352 with his thumb, pushing the inner cannula 334 toward the distal end 322. Alternatively, a thumb engaging outrigger 370, illustratively shown in FIG. 8, can be attached to the compression member 352 to facilitate thumb actuated movement of the inner cannula 334. When the inner cannula 334 covers the region of the notch 330, any tissue trapped in the interior region 328 is severed by the sharpened edge 342. This severed, dissected tissue can be drawn by surgical instruments, or preferably by suction pressure, through the inner cannula 334 through the longitudinal slots 346, through the third channel 318, and finally through the valve 340 to a storage or disposal site. Once the entrapped tissue has been severed and removed, the surgeon can release the thumb pressure on the compression member 352, allowing the return spring 358 to urge the inner cannula 334 to return to its rest position.

In the event that the wound from the severed tissue turns into a bleeder, a cauterizing device can be inserted into the inner cannula to cauterize the wound, if required. The compression member 352 is unthreaded from the annular projection 350 to open the central aperture 355 of the compressible annular seal 354. The cauterizing device is inserted through the compressible seal 354 toward the distal end 322 of the outer cannula. When the cauterizing device is positioned, the compression member 352 is screwed onto the annular projection 350 to close the central aperture 355, providing an airtight seal around the cauterizing device.

It will be appreciated that the cauterizing device could be inserted into the inner cannula 334 prior to commencement of the operation. Moreover, the tissue removal assembly 310 could be a pre-packaged assembly including the cauterizing device. However, to enhance the versatility of the assembly, it would be better to insert the cauterizing device when needed. That option leaves open the possibility of inserting other instruments such as graspers, laser vaporizers, or the like as necessary during the procedure.

An alternative embodiment, as illustrated in FIGS. 9 and 10, shows an inner cannula 434 having an open distal end 435. The inner cannula 434 is formed to include a notch 436 having a bevelled edge, with the notch 436 axially co-located with the notch 430 formed in the outer cannula 420. The edge of the notch 436 is bevelled inwardly as shown in FIG. 10 so as to form a sharpened edge 442 while the edge of the notch 430 is bevelled outwardly to form sharpened edge 443. In this embodiment, the inner cannula 434 is rotated rather than reciprocated inside the outer cannula 420. As the sharpened edge 442 of the notch 436 passes through the notch area 430, any tissue entrapped in the interior region is severed by the scissors-type movement between sharpened edges 442 and 443.

Figure 11:
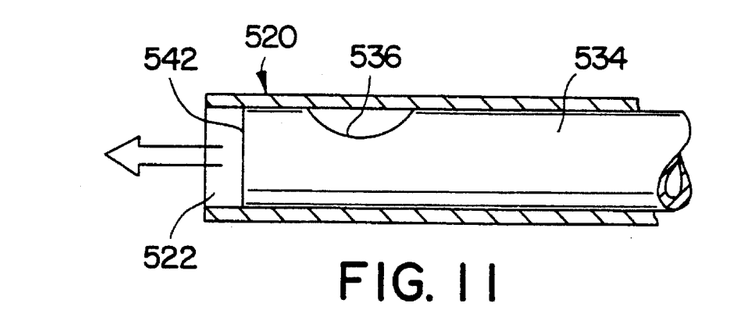
FIGS. 11–13 are three fragmentary views showing the cutting notch in the wall of the inner cannula with the inner cannula extendible out the open end of the outer cannula to be retracted inwardly during the cutting mode to use a scissors-type cutting action between the bevelled edge of the inner cannula notch and the distal end of the outer cannula.
Figure 12:
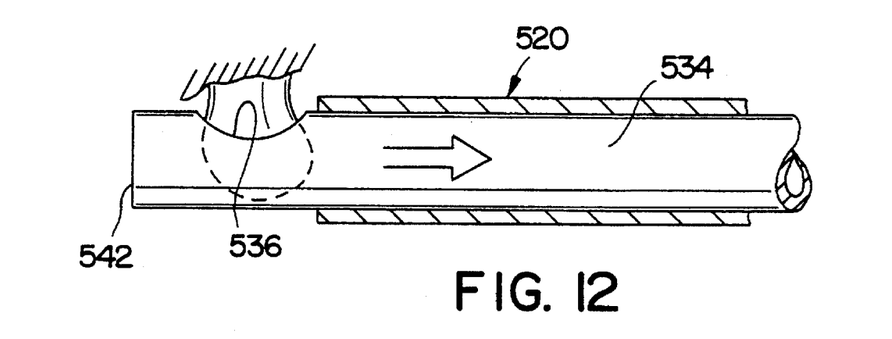
Figure 13:
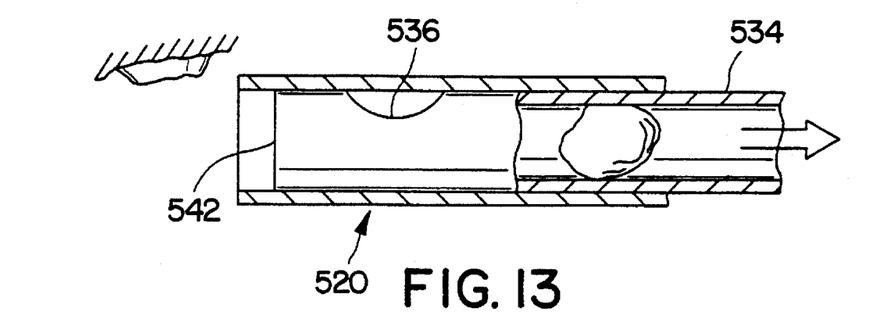

FIGS. 11–13 illustratively shows still another embodiment where the outer cannula 520 has an open end 522. The inner cannula 534 includes a distal end 542 and a notch 536 formed adjacent the distal end 542. The distal end 542 of the inner cannula 534 is preferably open so that instruments may be inserted through the inner cannula 534 and out through the open end 552.

FIG. 11 shows the inner cannula 534 in a normal rest position with the notch 536 positioned inside the outer cannula 520. When the inner cannula 534 is extended distally to expose the notch 536, tissue can be maneuvered into the notch 536, as shown in FIG. 12. As the inner cannula 534 is retracted, tissue trapped in the notch 536 is cut by the scissors-type action between the notch 536 and the distal end 522 of the outer cannula 520. Once severed, the tissue is drawn through the inner cannula 534, as shown FIG. 13, for analysis or disposal.

An irrigation and suction lavage assembly for removal of irrigation fluid and body tissue during laproscopy surgery can be seen generally with reference to FIGS. 14–18. The lavage assembly includes a conduit piece, inner and outer concentric cannulas coupled to the conduit piece, and means for moving the outer cannula relative to the inner cannula for cutting tissue. Breachable seals for sealing the inner cannula and the conduit piece are coupled to the inner cannula and the conduit piece, respectively. Valve means for controlling the flow of irrigation fluid and cut body tissue through the inner cannula and conduit piece is coupled to the conduit piece.

Figures 14, 15:
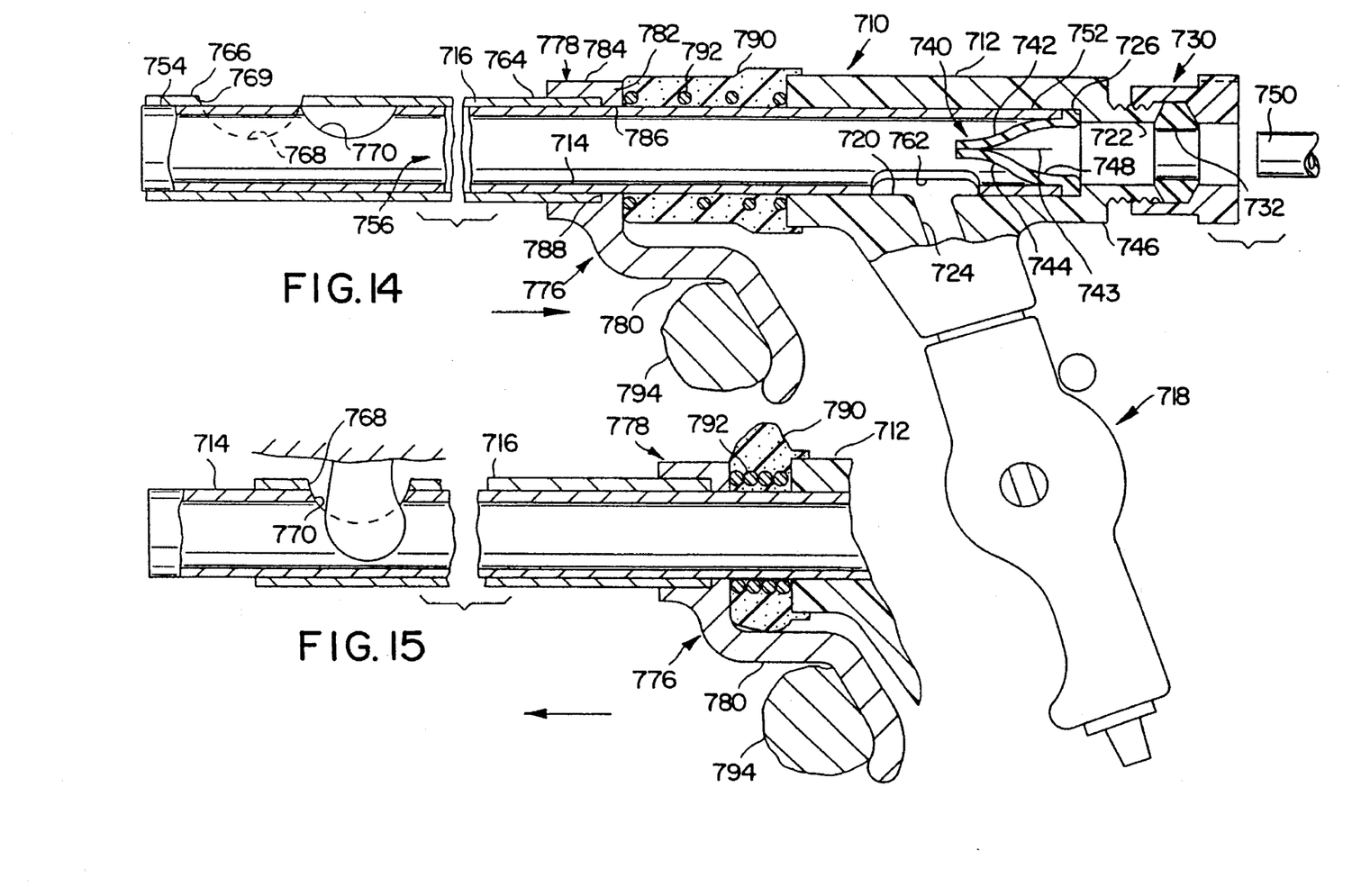
FIG. 14 is a side view of an alternative embodiment having an outer cannula that is movable relative to an inner cannula, wherein the outer cannula is retracted to align notches formed in the inner and outer cannulas and released to cut tissue trapped in the notches.
FIG. 15 is a view of the tip end of the embodiment of FIG. 14 showing the notches aligned to allow tissue to extend into the interior of the inner cannula in preparation for cutting.
Figure 16:
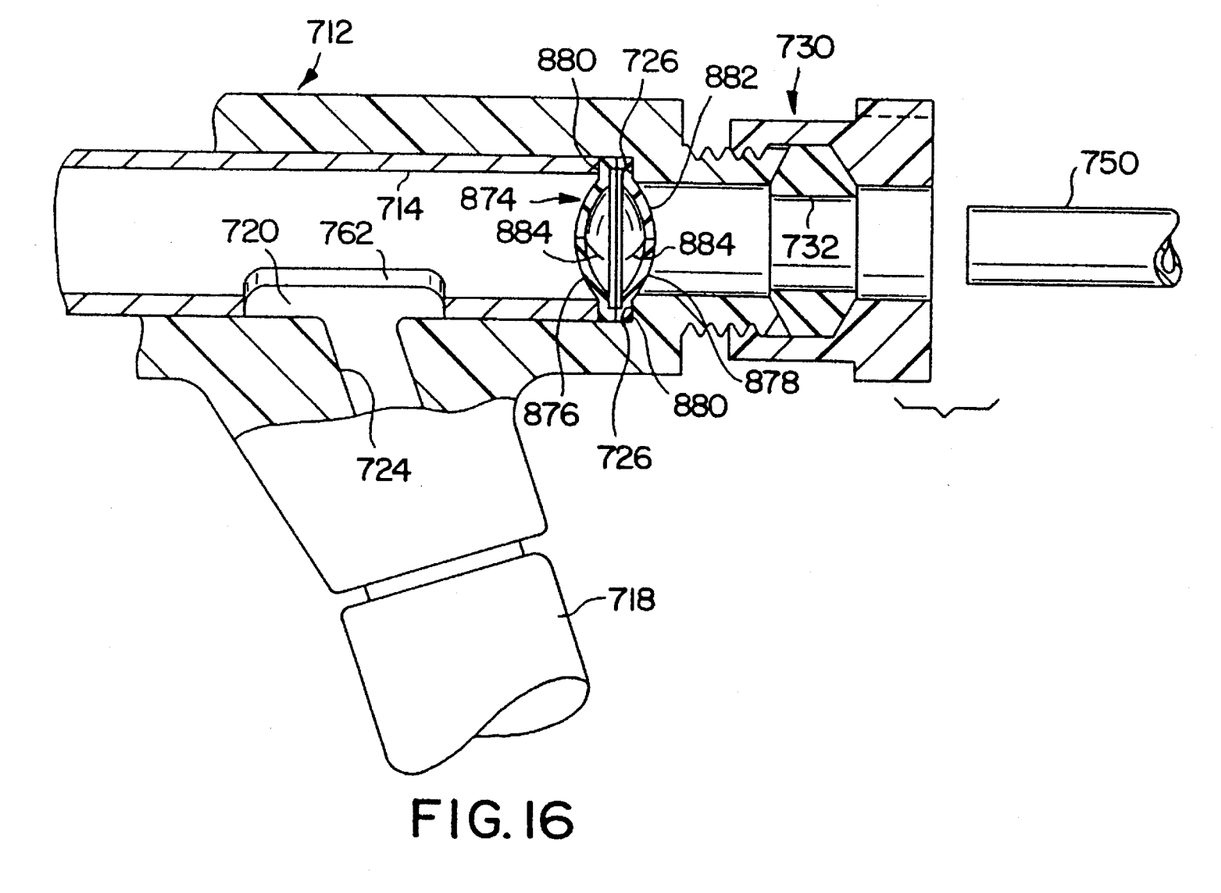
FIG. 16 shows a double duckbill flap valve as an alternative sealing means for breachably sealing the inner cannula.

As shown in FIGS. 14–16, the lavage assembly 10 includes a conduit piece 712, an inner cannula 714, and an outer cannula 716. The conduit piece 712 includes first, second, and third channels 720, 722, and 724, respectively. The first and second channels 720, 722 are coaxially aligned, with the distal end of the second channel 722 opening into the proximal end of the first channel 720. Illustratively, the second channel 722 has a smaller diameter than the first channel 720, thereby defining a shoulder 726 in the conduit piece 712 at the juncture between the first and second channels 720, 722. The third channel 724 intersects the first channel 720 and is in fluid communication with a valve 718.

A valve 718 is coupled to the assembly 710 to control the flow of fluids, gasses, and solids through the assembly 710. A preferred valve is described in U.S. Pat. No. 5,019,054 to Clement et al., and assigned to Mectra Labs, Inc., the disclosure of which is incorporated herein by reference.

The first and second channels 720, 722 are sealed by a duckbill flap valve 740 and a sealing mechanism 730, respectively. A preferred sealing mechanism 730 includes a compressible annular seal 732 and actuating mechanism as described in U.S. Pat. No. 5,456,636 to Clement and assigned to Mectra Labs, Inc., the disclosure of which is incorporated herein by reference.

The duckbill flap valve 740 is positioned in the first channel 720 and is situated in abutting relation to the shoulder 726. The duckbill flap valve 740 is integrally formed to have a first flap 742 biasingly directed in sealing engagement with a second flap 744. Both flaps 742 and 744 are integrally joined to an annular rim 746 having a central aperture 748 through which a medical device 750 can pass. The rim 746 projects radially outwardly from the flaps 742, 744 a distance equal to the thickness of the inner cannula 714 and is conformably fitted against the shoulder 726 and the wall of the first channel 720. The flaps 742 and 744 are separated by a slit 743 that allows the flaps 742 and 744 to separate, moving apart as the medical device 750 is inserted therethrough. The compressible annular seal 732 and the flaps 742 and 744 can be coated with friction reducing compounds to ease insertion or withdrawal of the medical device 750.

The inner cannula 714 has a proximal end 752, a distal end 754, and an interior region 756 extending therebetween. The proximal end 752 of the inner cannula 714 is coupled to the first channel 720 of the conduit piece 712. The outer diameter of the inner cannula 714 is substantially equal to the diameter of the first channel 720, allowing the inner cannula 714 to be inserted into the first channel 720. The inner cannula 714 is inserted until the proximal end 752 of the inner cannula 714 abuts the annular rim 746 formed on the duckbill flap valve 740, thereby holding the duckbill flap valve 740 in position against the shoulder 726. An elongated aperture 762 is formed in the inner cannula 714 and positioned to allow movement of gases, liquids and solids between the interior region 756 and the third channel 724. Any suitable fastening means can be used to attach the inner cannula 714 to the conduit piece 712, such as, welding, gluing or press-tight fit.

The outer cannula 716 is concentrically positioned to surround the inner cannula 714. The inner diameter of the outer cannula 716 is substantially equal to the outer diameter of the inner cannula 714 so as to provide a close, sliding engagement between the inner and outer cannulas 714, 716. The outer cannula 716 includes proximal and distal ends 764, 766, respectively. A first notch 768 is formed adjacent the distal end 766. The edge of the first notch 768 is bevelled outwardly from the outer cannula 716 so as to form a first cutting surface 769.

A second notch 770 is formed adjacent the distal end 754 of the inner cannula 714. The notches 768, 770 are normally positioned in a non-aligned relation to each other, so that access to the interior region 756 of the inner cannula 714 through the notches 768, 770 is barred.

The proximal end 764 of the outer cannula is coupled to a trigger means 776. The trigger means 776 includes a cup portion 778 for engaging the outer cannula 716 and an trigger portion 780 for engaging a digit 794 of a hand operating the removal assembly 710.

The annular cup portion 778 includes a circular base member 782 and a cylindrical side wall 784. The inner diameter of the cylindrical sidewall 784 is substantially equal to the outer diameter of the outer cannula 716. The circular base member 782 includes a central aperture 786 having a diameter substantially equal to the outer diameter of the inner cannula 714. Thus, the circular base member 782 and the cylindrical side wall 784 cooperate to form a shoulder 788. The outer cannula 716 is inserted into the trigger means 776 until the proximal end 764 of the outer cannula 716 abuts the shoulder 788. The now-joined outer cannula 716 and trigger means 776 can slidably engage the inner cannula 714 as a unit. The trigger 780 provides a means for engaging the digit 794 of the surgeon's hand.

A cylinder 790 of elastomeric material surrounds the inner cannula 714, but is not attached thereto. The cylinder 790 is attached to the trigger means 776 and the conduit piece 712, thereby coupling the trigger means/outer cannula 776, 716 to the conduit piece 712. A compression spring 792 is embedded in the cylinder 790 of elastomeric material.

In operation, distal ends 754,766 of the inner and outer cannulas 714, 716, respectively, of the irrigation and suction lavage assembly 710 are inserted into a patient's body by conventional means. When the lavage assembly 710 is properly positioned at the operating site, the surgeon rotates the valve 718 in a first direction to permit saline solution or other irrigation fluid to flow to the site. When the site is sufficiently clear, the surgeon can turns off the irrigation fluid and pull the trigger 780. Pulling the trigger 780 moves the trigger means/outer cannula 776/716 away from the normal, or rest, configuration in the direction of arrow 795 (FIG. 14). As the outer cannula 716 slides along the inner cannula 714, the notches 768, 770 align to permit tissue 771 to enter the interior region 756, as shown in FIG. 15.

When the trigger means 776 is pulled in the direction of arrow 795, the cylinder 790 of elastomeric material and the spring 792 are compressed between the trigger means 776 and the distal end of the conduit piece 712, storing mechanical energy. When the notches 768, 770 have been aligned, tissue 771 can be maneuvered into the interior region 756 through the aligned notches 768, 770. Once the tissue 771 has been maneuvered into the notches 768, 770, the trigger means 776 is disengaged, thereby releasing the stored mechanical energy to restore the cylinder 790 of elastomeric material and the spring 792 to their original states and move the outer cannula 716 in the direction of arrow 797 (FIG. 15) to its normal, or rest, position.

As the outer cannula 716 moves, the cutting surfaces of the notches 768, 770 move relative to each other, thereby cutting the tissue 771 trapped in the interior region 756. The surgeon rotates the valve 718 in a second direction to connect a vacuum source (not shown) to the inner cannula 714 through the first and third channels 720, 724, respectively. The vacuum draws the cut tissue through the interior region 756, the elongated aperture 762 in the inner cannula 714, and the third channel 724. Once removed, the cut tissue can be stored for later analysis or disposal.

When the tissue 771 is cut, the resulting wound could by a bleeder. In that case, it would be advantageous to be able to present an electro-cautery device to the site of the wound. An electro-cautery device, or other medical instrument 750, can be inserted through the compressible annular seal 732 and the duckbill flap valve 740 to be presented at the distal end 754 of the inner cannula 714. The distal end 754 can be maneuvered to position the electro-cautery device at the tissue removal site to cauterize the injury. Advantageously, the sealing mechanism 730 and the duckbill flap valve 740 cooperate to prevent ingassing or outgassing of fluids through the second channel 722 during the procedure.

Figures 17, 18:
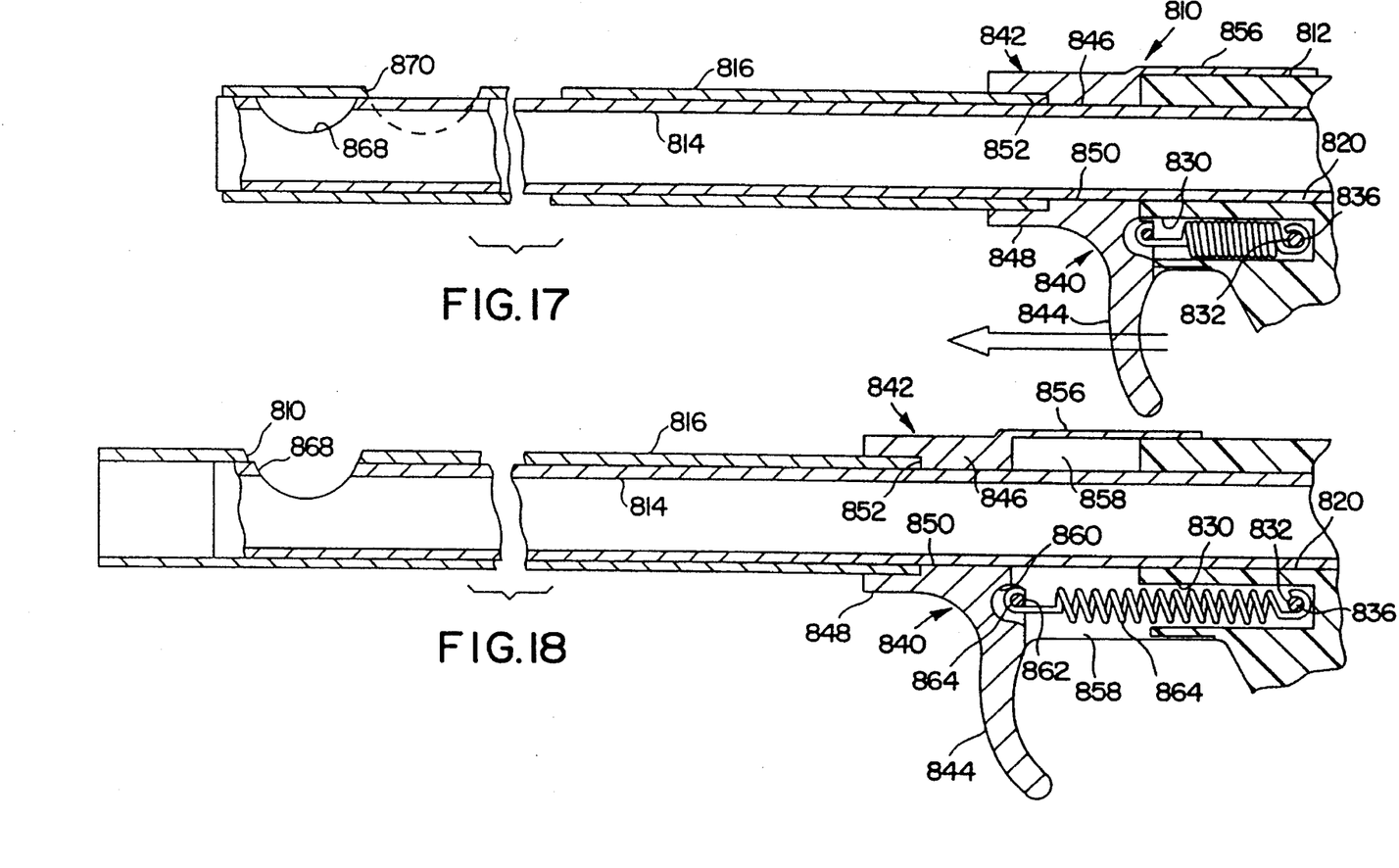
FIG. 17 shows an alternative embodiment having an outer cannula that is movable relative to an inner cannula, wherein the outer cannula is extended to align notches formed in the inner and outer cannulas and is released to cut tissue trapped in the notches.
FIG. 18 shows the embodiment of FIG. 17 with the outer cannula extended and the notches aligned for receiving tissue.

The embodiment of FIGS. 17–18 provides for reversing the cutting action of the outer cannula. When the lavage assembly 810 is in the normal or rest position as illustrated in FIG. 17, the notch 870 in the outer cannula 816 is positioned proximal to the notch 868 in the inner cannula 814 in contradistinction to the arrangement of FIG. 14. Thus, the outer cannula 816 is moved axially away from the conduit piece 812 relative to the inner cannula 814 in order to align the notches 868, 870.

The conduit piece 812 is substantially similar to the conduit piece 712 in FIGS. 14–16, but includes first and second holes 830, 832 bored into the conduit piece 812. The first hole 830 is bored into the distal end of the conduit piece 812 to lie parallel to the axis Of the first channel 820 of the conduit piece 812. The second hole 832 is bored transversely through the conduit piece 812 to perpendicularly intersect the first hole 830 and receive a first spring retaining dowel 836.

The inner and outer cannulas 814, 816, respectively, are substantially similar to the cannulas in FIGS. 14–16. The trigger means 840 includes an annular cup portion 842 and an outrigger portion 844. The annular cup portion 842 includes a circular base member 846 and a cylindrical side wall 848. The inner diameter of the sidewall 848 is substantially equal to the outer diameter of the outer cannula 816 so as to provide a tight fit. The circular base member 846 includes a central aperture 850 having a diameter substantially equal to the outer diameter of the inner cannula 814. Thus, the circular base member 846 and the cylindrical side wall 848 cooperate to form a shoulder 852 in the cup portion 842. The proximal end of the outer cannula 816 snugly fits inside the cylindrical side wall 848 and abuts the shoulder 852 in the cup portion 842. The outer cannula 816 is rigidly attached to the trigger means 840 by welding, gluing, or other suitable attaching means. The now-joined outer cannula 816 and trigger means 840 slidingly engage the inner cannula 814.

The trigger means 840 in the embodiment of FIGS. 17–18 also includes a skirt portion 856 extending proximally from the circular base member 846. The skirt portion 856 is configured to conform to the general shape of, and extend beyond, the distal end of the conduit piece 812 to partially surround the conduit piece 812. The skirt portion 856 is configured to allow the trigger means 840 and outer cannula 816 to slide along the inner cannula 814 while enclosing the space 858 (FIG. 18) between the circular base portion 846 and the distal end of the conduit piece 812.

A third hole 860 is bored into the trigger means 840 at the juncture between the cup portion 842 and the trigger portion 844 so as to be coaxially aligned with the first hole 830 in the conduit piece 812. The diameter of the third hole 860 is substantially equal to the diameter of the first hole 830. A fourth hole 862 is bored transversely into the trigger means 840 so as to perpendicularly intersect the third hole 860. The fourth hole 862 receives a second spring retaining dowel 864.

An expansion spring 866 extends between the first and third holes 830, 860, respectively, and is retained in position by the first and second spring retaining dowels 836, 864, respectively. Thus, the expansion spring 866 resiliently couples the outer cannula 816 to the conduit piece 812.

The inner and outer cannulas 814, 816 each include a notch 870, 868, respectively, formed in the distal ends thereof. In the embodiment of FIGS. 17–18, however, the relative positions of the notches 868, 870 are reversed as compared to the embodiment of FIGS. 14–15. That is, in FIGS. 17–18, the notch 868 in the inner cannula 814 is distal to the notch 870 in the outer cannula 816. Thus, the embodiment of FIGS. 17–18 operates essentially oppositely to the embodiment of FIGS. 14–15.

In operating the embodiment of FIGS. 17–18, the operator engages the outrigger portion 844 so as to slide the outer cannula 816 from its normal, or rest, position in the direction of arrow 872 (FIG. 17) in order to align the notches 868, 870. The spring 866 is extended to store mechanical energy. When the notches 868, 870 are aligned, tissue is maneuvered into the interior region of the inner cannula 814. When the tissue has been maneuvered through the notches 868, 870, the outrigger portion 844 can be disengaged to release the spring 866. The released mechanical energy causes the spring 866 to pull the outer cannula 816 in the direction of arrow 874 (FIG. 18) back to its normal, or rest, position and cutting any tissue trapped in the notches 868, 870.

It will be appreciated that the means for cutting tissue formed on the inner cannula 814 could be a sharpened edge substantially similar to the sharpened edge 342 discussed with reference to FIG. 7. without exceeding the scope of the invention. In such an embodiment, the outer cannula 816 would be extended by pushing on the outrigger portion 844 so that the notch 868 extends beyond the sharpened edge, and the tissue would be cut by the sharpened edge as the outrigger portion 844 is released.

While the preceeding discussion focused on reciprocating the outer cannula relative to the inner cannula, it will be appreciated that the outer cannula can be rotated relative to the inner cannula without exceeding the scope of the invention. Rotational relative movement would cut tissue as previoulsy described with reference to FIGS. 9 and 10.

FIG. 16 shows another embodiment of the duckbill flap valve in the form of a double duckbill valve 874 for use in the embodiments of FIGS. 14–15 and 17–18. The double duckbill valve 874 includes two domed duckbills 876 and 878. The domed duckbills 876 and 878 are formed to include circumferential flanges 880 extending axially from domed center portions 882. The duckbills 876 and 878 are operably positioned in back-to-back relation so that the flanges 880 abut each other and the domed center portions 882 cooperate to define a convex shape, as shown illustratively in FIG. 16. Each domed duckbill 876, 878 also includes a slit 884 formed in the domed center portion 882 to allow the passage of a medical instrument 750 through the double duckbill valve 874.

As in the duckbill flap valve 740 of FIGS. 14–15, the flanges 880 extend radially outwardly from the domed center portions 882 a distance equal to the thickness of the inner cannula 714. Thus, when inserted into the first channel 720, the inner cannula 714 holds the double duckbill flap valve 874 in position by pinching the flanges 880 between the proximal end of the inner cannula 714 and the shoulder 726.

Use of a double duckbill 874 provides several advantages. First, the double duckbill 874 is a two-way valve, whereas conventional duckbill valves are one-way. That is, the double duckbill 874 prevents entry of atmosphere into, as well as escape of fluids from, the body of the patient. Second, use of two identical valves in a back-to-back relation simplifies the manufacturing and assembly process and reduces inventory management requirements.

Although the invention has been described in detail with reference to certain preferred embodiments, variations and modifications exist within the scope and spirit of the invention as described and defined in the following claims.

I claim:

1. An irrigation and suction lavage assembly for irrigation and removal of irrigation fluid and body tissue during surgery, the assembly being operable by one hand of a surgeon, the assembly comprising:

a conduit piece;

an inner cannula defining an interior region and having a distal end, first means formed adjacent the distal end for cutting tissue, and a proximal end rigidly coupled to the conduit piece;

valve means coupled to the conduit piece for controlling the flow of irrigation fluid and body tissue through the conduit piece and the inner cannula; and an outer cannula having a distal end and second means formed adjacent the distal end for cutting tissue, the inner cannula being coaxially positioned inside the outer cannula, the first and second cutting means being axially positioned to cut tissue in response to movement of the outer cannula.

2. The assembly of claim 1, wherein the outer cannula is resiliently coupled to the conduit piece for movement relative to the inner cannula.

3. The assembly of claim 2, wherein the outer cannula includes means for engaging a digit of the surgeon's hand to permit one-handed movement of the outer cannula by the surgeon.

4. The assembly of claim 3, wherein the engaging means includes resilient means for coupling the engaging means to the conduit piece and a trigger for engaging a digit of a surgeon's hand, the trigger being pulled toward the conduit piece and released to reciprocate the outer cannula, the resilient means urging the outer cannula away from the conduit piece in response to release of the trigger.

5. The assembly of claim 3, wherein the engaging means includes resilient means for coupling the engaging means to the conduit piece and an outrigger for engaging a digit of a surgeon's hand, the outrigger being pushed away from the conduit piece and released to reciprocate the outer cannula, the resilient means urging the outer cannula toward the conduit piece in response to release of the outrigger.

6. The assembly of claim 1, wherein the first cutting means includes a first notch formed adjacent a distal end of the inner cannula and the second cutting means includes a second notch formed adjacent a distal end of in the outer cannula, the first and second notches being alignable to allow tissue to enter the interior region through the notches, the first and second notches cooperating to cut the entered tissue in response to movement of the first notch past the second notch.

7. The assembly of claim 1, further comprising first means coupled to the proximal end of the inner cannula for breachably sealing the proximal end of the inner cannula to allow a surgical instrument to be sealingly inserted into the inner cannula.

8. The assembly of claim 7, wherein the conduit piece includes a channel, the assembly further comprising second means coupled to the channel for sealing the channel to allow a surgical instrument to be sealingly inserted into the channel and the inner cannula.

9. The surgical assembly of claim 1, wherein the valve means is located in the conduit piece.

10. An irrigation and suction lavage assembly for irrigation and removal of irrigation fluid and body tissue during surgery, the assembly being operable by one hand of a surgeon, the assembly comprising:

a conduit piece;

an inner cannula defining an interior region and having a distal end, first means formed adjacent the distal end for cutting tissue, the inner cannula being coupled to the conduit piece;

valve means coupled to the conduit piece for controlling the flow of irrigation fluid and body tissue through the conduit piece and the inner cannula; and an outer cannula having a distal end and second means formed adjacent the distal end for cutting tissue, the inner cannula being coaxially positioned inside the outer cannula, the first and second cutting means being axially positioned to cut tissue in response to reciprocating movement of the outer cannula; and means coupled to the outer cannula for engaging a digit of the surgeon's hand to allow the surgeon to move the outer cannula relative to the inner cannula.

11. The assembly of claim 10, wherein the engaging means is resiliently coupled to the conduit piece and includes means for storing mechanical energy during movement of the outer cannula relative to the inner cannula.

12. The assembly of claim 11, wherein the storing means is configured to store energy when the engaging means is pulled toward the conduit piece by the surgeon and to release the stored mechanical energy upon disengagement of the engaging means by the surgeon.

13. The assembly of claim 11, wherein the storing means is configured to store energy when the engaging means is pushed away from the conduit piece by the surgeon and to release the stored mechanical energy upon disengagement of the engaging means by the surgeon.

14. The assembly of claim 10, further comprising first means coupled to a proximal end of the inner cannula for breachably sealing the proximal end of the inner cannula to allow a surgical instrument to be sealingly inserted into the inner cannula.

15. The assembly of claim 14, wherein the conduit piece includes a channel, the assembly further comprising second means coupled to the channel for sealing the channel to allow a surgical instrument to be sealingly inserted into the channel and the inner cannula.

16. The surgical assembly of claim 10, wherein the valve means is located in the conduit piece.

17. An irrigation and suction lavage assembly for irrigation and removal of irrigation fluid and body tissue during surgery, the assembly comprising:

an outer cannula having a side wall defining a first cutting surface for cutting tissue, the outer cannula being movable between a rest position and a ready-for-cutting position;

an inner cannula coaxially positioned inside the outer cannula and having a proximal end, the inner cannula defining an interior region and having a second cutting surface;

first means coupled to a proximal end of the inner cannula for breachably sealing the proximal end to allow a surgical instrument to be sealingly inserted into the inner cannula;

valve means coupled to the inner cannula for controlling the flow of irrigation fluid and body tissue through the inner cannula; and means coupled to the outer cannula for moving the outer cannula relative to the inner cannula in response to movement of a digit of the surgeon's hand to cut tissue.

18. The assembly of claim 17, further comprising resilient means coupled to the moving means and the outer cannula for moving the outer cannula to the rest position from the ready-to-cut position.

19. The assembly of claim 18, wherein the moving means includes a trigger for engaging the first digit of the surgeon's hand, the trigger being configured to be pulled toward the conduit piece to move the outer cannula from the rest position to the ready-to-cut position.

20. The assembly of claim 17 further comprising means for actuating the valve means by movement of a second digit of the surgeon's hand.

21. The assembly of claim 17, wherein the valve means includes a valve body housing a valve therein, the valve body being shaped to have a manually grippable body and form a pistol grip, wherein said valve body defines a channel extending therethrough in fluid communication with the inner cannula.

22. The surgical assembly of claim 17, wherein the valve means is located in the conduit piece.

23. A surgical assembly for removal of body tissue, the assembly comprising: a rigid outer cannula defining a cannula interior, the cannula having a proximal end and a distal end, the distal end being insertible and positionable into a patient's body, and the cannula defining a cutting surface opening adjacent the distal end to permit access to the cannula interior for capture of body tissue in the cannula interior, the rigidity of the cannula causing the distal end thereof to move in the same direction and distance as the proximal end;

a rigid inner cannula with a cutting surface and passageway therein, said inner cannula supporting the outer cannula and having its cutting surface cooperate with the cutting surface of the rigid outer cannula for cutting body tissue;

means for moving the outer cannula relative to the inner cannula;

a conduit piece rigidly attached to the inner cannula which supports the outer cannula for movement, the conduit piece having at least one channel defined therein in fluid communication with the cooperating cutting surface on the outer and inner cannula;

moveable valve means rigidly coupled to the rigidly attached conduit piece and inner cannula for controlling flow through said one channel;

the rigidly coupled conduit piece and valve means having a handgrip portion for holding and accurately positioning the distal end of the inner cannula at a desired location in the patient by movement of the handgrip portion to direct the distal end of the inner cannula to the desired location; suction means connected to the at least one channel for removing body tissue cut by the cutting surface through the cannula and conduit piece;

mean to move the valve means;

wherein both the means for moving the cutter and the valve means can be actuated by a digit of the hand gripping the hand grip portion while the hand moves the rigidly attached conduit piece and inner cannula to position the distal end of the inner cannula at the desired location in the patient.

24. The surgical assembly of claim 23, wherein the means to move the outer cannula is resiliently biased to position the cutting surfaces into a non-cutting position such that a push action against the resilient bias moves the cutter for cutting.

25. The surgical assembly of claim 23, wherein the hand grip portion for rigidly gripping the rigidly coupled valve means and conduit piece is a surface surrounding the valve means.

26. The surgical assembly of claim 24, wherein the hand grip portion for rigidly gripping the rigidly coupled valve means and conduit piece is a surface surrounding the valve means.

27. The surgical assembly of claim 23, wherein the valve means is located in the conduit piece.

28. The surgical assembly of claim 24, wherein the valve means is located in the conduit piece.

29. The surgical assembly of claim 25, wherein the valve means is located in the conduit piece.

30. The surgical assembly of claim 25, wherein the valve means is located in the conduit piece.

31. The surgical assembly of claim 23, wherein the valve means also controls flow of irrigation fluid to the patient through said one channel.

32. The surgical assembly of claim 24, wherein the valve means also controls flow of irrigation fluid to the patient through said one channel.

33. A lavage assembly for surgery, irrigation, suction, and removal of body tissue, the assembly comprising:

a rigid cannula defining a cannula interior, the cannula having a proximal end and a distal end, the distal end being insertible and positionable in a patient's body, and the cannula defining a cannula opening adjacent the distal end to permit access to the cannula interior for capture of body tissue in the cannula interior;

a cutter moveable outside the cannula interior for cutting body tissue entering the cannula opening;

means for moving the cutter;

an independently actuated vane means rigidly connected to the cannula to control irrigation and suction flow to the cannula interior, regardless of movement or lack of movement of the cutter;

means to actuate the valve means;

wherein the cannula and valve means are integrated into a rigid structure to be held in one hand such that movement of the rigidly coupled valve means and cannula by a users hand allows the distal end of the cannula to be accurately positioned at a specific location in the patients body; and wherein the means for moving the cutter and the means to actuate the valve means are both operable by a hand of the user as it moves the rigidly coupled valve means and cannula to accurately position the distal end of the cannula in the patient.

34. The surgical assembly of claim 33, wherein the means to move the cutter is resiliently biased to position the cutter into a non-cutting position such that a push action against the resilient bias moves the cutter for cutting.

35. The surgical assembly of claim 33, wherein there is a hand grip portion for the rigidly coupled valve means and cannula, which hand grip portion is a surface surrounding the valve means.

36. The surgical assembly of claim 34 wherein there is a hand grip portion for the rigidly coupled valve means and cannula, which hand grip portion is a surface surrounding the valve means.

37. The surgical assembly of claim 33 wherein the cannula supports the cutter.

38. The surgical assembly of claim 34 wherein the cannula supports the cutter.

39. The surgical assembly of claim 35 wherein the cannula supports the cutter.

40. The surgical assembly of claim 36 wherein the cannula supports the cutter.

41. The surgical assembly of claim 33 wherein the cannula has an opened distal end to allow communication between the cannula interior and the patient.

42. The surgical assembly of claim 34 wherein the cannula has an opened distal end to allow communication between the cannula interior and the patient.

43. The surgical assembly of claim 35 wherein the cannula has an opened distal end to allow communication between the cannula interior and the patient.

44. The surgical assembly of claim 36 wherein the cannula has an opened distal end to allow communication between the cannula interior and the patient.

45. The surgical assembly of claim 37 wherein the cannula has an opened distal end to allow communication between the cannula interior and the patient.

46. The surgical assembly of claim 38 wherein the cannula has an opened distal end to allow communication between the cannula interior and the patient.

47. The surgical assembly of claim 39 wherein the cannula has an opened distal end to allow communication between the cannula interior and the patient.

48. The surgical assembly of claim 40 wherein the cannula has an opened distal end to allow communication between the cannula interior and the patient.

\* \* \* \* \*